United States Patent [19]

Suzuki et al.

[11] Patent Number: 5,317,095
[45] Date of Patent: May 31, 1994

[54] ALPHA-D-GLYCOSYL KASUGAMYCIN, ITS PREPARATION, AND ANTIBACTERIAL AGENT CONTAINING THE SAME

[75] Inventors: Yukio Suzuki; Koutarou Muroyama; Kei Suzuki, all of Kurashiki, Japan

[73] Assignee: Hayashibara Biochemical Laboratories, Inc., Okayama, Japan

[21] Appl. No.: 25,755

[22] Filed: Mar. 3, 1993

[30] Foreign Application Priority Data

Sep. 1, 1992 [JP] Japan .................................. 4-233512

[51] Int. Cl.$^5$ ...................... C07H 17/04; C12P 19/46
[52] U.S. Cl. ..................................... 536/16.7; 435/79; 435/201; 435/931
[58] Field of Search ................. 536/16.7; 435/79, 201, 435/931

[56] References Cited

FOREIGN PATENT DOCUMENTS 42-6818 3/1967 Japan .
63-56202 11/1988 Japan .
1-33447 7/1989 Japan .

OTHER PUBLICATIONS

Chem Abs. vol. 70 No. 3:17739r Fukagawa et al. (1969) abs. of "J. Antibiot" (Tokyo) 1968, 21(5) 358–60 (Eng.).
Chem. Abs. vol. 17 No. 17:75892e Fukagawa et al. (1970) abs. of "J. Antibiot" (Tokyo) 1968 21(1), 50–4 (1968) (Eng.).

Primary Examiner—Herbert J. Lilling
Attorney, Agent, or Firm—Armstrong, Westerman, Hattori, McLeland & Naughton

[57] ABSTRACT

An α-D-hlycosyl kasugamycin having the formula (III):

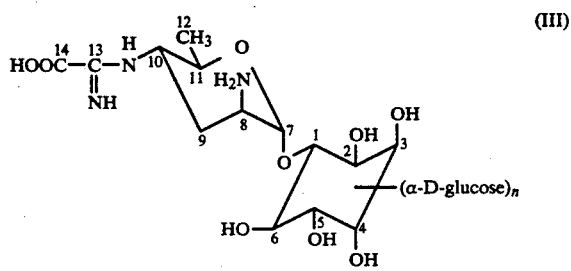

wherein n is an integer of not less than 1.

According to the present invention, the novel substance which is highly safe and easily hydrolyzed with α-glucosidase to exhibit physiological activities inherent to kasugamycin is obtained.

4 Claims, 2 Drawing Sheets

ALPHA-D-GLYCOSYL KASUGAMYCIN, ITS PREPARATION, AND ANTIBACTERIAL AGENT CONTAINING THE SAME

BACKGROUND OF THE INVENTION

The present invention relates to an α-D-glycosyl kasugamycin and its preparation, and an antibacterial agent containing the same; more particularly, to a novel substance, an α-D-glycosyl kasugamycin exhibiting an antibacterial activity, to a process which comprises allowing a saccharide-transferring enzyme to act on an amylaceous substance and kasugamycin to form α-D-glycosyl kasugamycin and recovering said α-D-glycosyl kasugamycin, and to an antibacterial agent which contains α-D-glycosyl kasugamycin.

Kasugamycin is an antibiotic that is produced by a microorganism of the species, Streptomyces kasugaensis as disclosed in Japanese Examined Patent Publication No. 6818/1967, and has the chemical structure shown by the following formula (I):

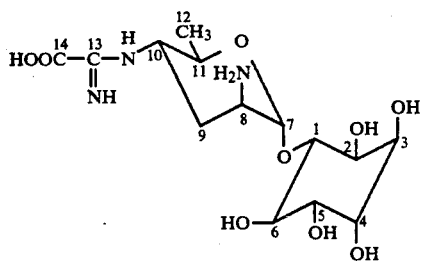

Because of its activity of inhibiting the growth of pathogenic microorganisms proliferating in plants, fishes, domestic animals and poultries, kasugamycin is utilizable as an antibacterial agent applicable to agriculture and gardening or fishery and farming, for example, as disclosed in Japanese Examined Patent Publications No. 56202/1988 and No. 33447/1989.

In general, antibiotics cause a trouble of the emergence of resistant bacterium and there has been a great demand to establish a highly safe derivative of kasugamycin.

An object of the present invention is to provide a novel highly safe derivative of kasugamycin which exhibits an antibacterial activity inherent to kasugamycin.

Another object of the present invention is to provide a process for preparing the derivative.

Further object of the present invention is to provide an antibacterial agent containing the derivative.

These and other objects will become apparent from the description hereinafter.

SUMMARY OF THE INVENTION

The present invention provides an α-D-glycosyl kasugamycin having the formula (III):

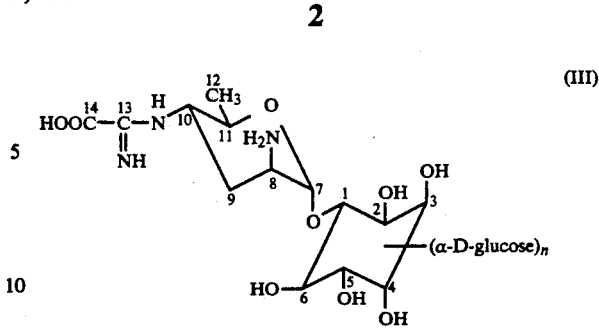

wherein n is an integer of not less than 1 and D-glucoses are joined by a α 1, 4 glycosidic linkage.

Further the present invention provides a process for preparing an α-D-glycosyl kasugamycin having formula (III), which comprises:

(a) allowing a saccharide-transferring enzyme to act on a solution containing kasugamycin and an amylaceous substance to form an α-D-glycosyl kasugamycin; and (b) recovering the α-D-glycosyl kasugamycin.

Furthermore the present invention provides an antibacterial agent comprising an effective amount of an α-D-glycosyl kasugamycin having the formula (III).

It has now been found that the novel substance, α-D-glycosyl kasugamycin according to the invention has excellent water-solubility and stability, and is hydrolyzed by a α-glucosidase into kasugamycin and D-glucose to exhibit the inherent physiological properties of kasugamycin.

Furthermore, this α-D-glycosyl kasugamycin can be readily obtained by the biochemical method comprising a step of allowing a saccharide-transferring enzyme together with or without a glucoamylase to act on a solution containing and an amylaceous substance. Thus, a α-D-glycosyl kasugamycin is superior in economical efficiency and commercialization of α-D-glycosyl kasugamycin is easy.

Thus, α-D-glycosyl kasugamycin can be favorably used as a highly safe antibacterial agent in agriculture, gardening, domestic animal feeding and pet fishing.

BRIEF DESCRIPTION OF THE DRAWINGS

In FIG. 2(A), G-1 exhibits the carbon at 1-position of α-D-glucose, G-3 exhibits the carbon at 3-position of α-D-glucose, and G-6 exhibits the carbon at 6-position of α-D-glucose.

DETAILED DESCRIPTION

Figure 1:
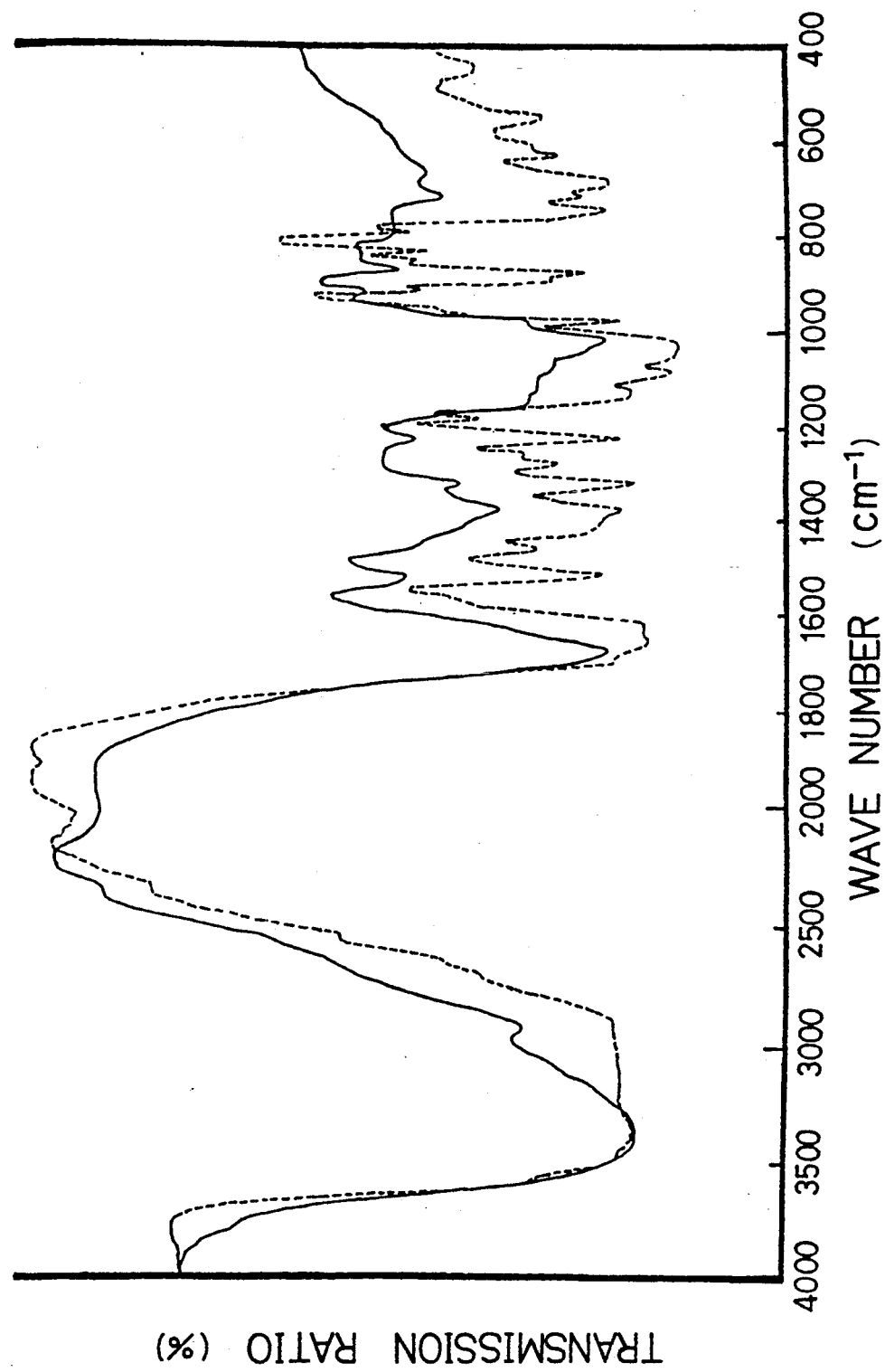
FIG. 1 shows an infrared absorption spectrum of an α-D-glucosyl kasugamycin as an example of the kasugamycin derivative and that of kasugamycin as a comparative example.

It has been found that the present α-D-glycosyl kasugamycin is a desirable substance which is highly safe and easily hydrolyzed with a α-glucosidase to exhibit physiological activities inherent to kasugamycin.

It has been found that the present α-D-glycosyl kasugamycin can be prepared by allowing a saccharide-transferring enzyme to act on a solution containing kasugamycin and an amylaceous substance to form α-D-glycosyl kasugamycin, and recovering the α-D-glycosyl kasugamycin.

The wordings "kasugamycin", "α-D-glycosyl kasugamycin" and "α-D-glucosyl kasugamycin" as referred to in the invention are intended to mean those which include salts thereof, for example, hydrochloride of kasugamycin, α-D-glycosyl kasugamycin and α-D-glucosyl kasugamycin, respectively, as long as there is no inconvenience.

The kasugamycin used in the invention, is in a purified state. If necessary, intact or partially purified culture of microorganisms, such as these of the genus Streptomyces, wherein kasugamycin had been produced can be suitably used.

The amylaceous substances usable in the present invention are those which can form α-D-glycosyl kasugamycin, such as α-D-glucosyl kasugamycin, α-D-maltosyl kasugamycin, α-D-maltotriosyl kasugamycin, and α-maltotetraosyl kasugamycin, wherein equimolar or more glucose residues are linked to kasugamycin via the action of the saccharide-transferring enzyme simultaneously used. The amylaceous substances include starches and modified starches. Examples of the amylaceous substances are partial hydrolysates of starch such as amylose, dextrin, cyclodextrin and maltooligosaccharide, and liquefied starch and gelatinized starch, and the like.

Additionally, to facilitate the preparation of α-D-glycosyl kasugamycin, amylaceous substances which are suitable for the used saccharide-transferring enzyme are chosen.

For instance, in the case of using α-glucosidase (EC 3.2.1.20) as the saccharide-transferring enzyme, maltooligosaccharide such as maltose, maltotriose or maltotetraose, or a partial hydrolysate of starch having a Dextrose Equivalent (hereinafter referred to as "DE") in the range from about 10 to about 70 is preferable. When cyclomaltodextrin glucanotransferase (EC 2.4.1.19) is used as the saccharide-transferring enzyme, cyclodextrin or a gelatinized starch having a DE not more than 1 and a partial hydrolysate of starch having a DE of up to about 60 are suitable. When α-amylase (EC 3.2.1.1) is used as the saccharide-transferring enzyme, a gelatinized starch having a DE not more than 1, or a dextrin or a partial hydrolysate of starch having a DE of up to about 30 is suitable.

The solution containing kasugamycin and an amylaceous substance usable in the invention is that which contains kasugamycin at the highest possible level. More particularly, examples of such a solution are those which are obtainable by dissolving kasugamycin under an acidic pH of lower than 7.0 to give a kasugamycin content of not less than about 1.0 w/v %, desirably, from about 5.0 to about 20.0 w/v %.

The saccharide-transferring enzymes usable in the invention are those which catalyze the reaction producing α-D-glycosyl kasugamycin in a solution containing kasugamycin and an amylaceous substance suitable for said saccharide-transferring enzyme without decomposing kasugamycin. Examples of such a saccharide-transferring enzyme are α-glucosidases derived from affimal or plant tissues such as pig liver, seeds of buckwheat or rice plants, and α-glycosidases derived from cultures obtained by cultivating in a nutrient culture medium microorganisms including, molds and yeasts, for example, those of the genera Mucor, Penicillium and Saccharomyces; cyclomaltodextrin glucanotransferases derived from cultures of bacteria such as those of the genera Bacillus and Klebsiella; and α-amylase derived from cultures of bacteria such as those of the genus Bacillus, and cultures of fungus such as those of the genus Aspergillus.

It is not necessary that the saccharide-transferring enzyme is purified prior to its use, as long as it fulfills the above requirements. Generally, the present invention is feasible with a crude enzyme. If necessary, the saccharide-transferring enzyme can be purified by conventional methods, prior to its use. Of course, commercially available saccharide-transferring enzymes can be used in the invention.

In the course of the reaction, the pH and the temperature are set to respective levels at which kasugamycin is stable and α-D-glycosyl kasugamycin is produced, for example, a pH in the range from 3.0 to 7.0 and a temperature in the range from 10° to 90° C., preferably, a pH in the range from 4.0 to 6.5 and a temperature in the range from 40° to 75° C.

The reaction time are closely dependent on the amount of saccharide-transferring enzyme. Usually, from an economical viewpoint, saccharide-transferring enzyme is used in such an amount that the reaction is completed within about 5 to about 80 hours.

Immobilized saccharide-transferring enzymes can be suitably used batchwise.

If necessary, α-D-glycosyl kasugamycin can be produced by culturing a microorganism, or an animal- or plant-tissue capable of producing a saccharide-transferring enzyme in a culture medium which contains an amylaceous substance and kasugamycin.

According to the process of the present invention, α-D-glycosyl kasugamycin can be prepared by allowing a saccharide-transferring enzyme or a saccharide-transferring enzyme together with glucoamylase (EC 3.2.1.3) to act on a solution which contains kasugamycin and an amylaceous substance.

A glucoamylase derived from microorganisms or plants can be used in the above process. Examples of such a glucoamylase are conunercially available glucoamylases derived from microorganisms of the genera Aspergillus and Rhizopus.

For effectively utilizing a saccharide-transferring enzyme, it is preferable that a solution containing kasugamycin and an amylaceous substance is first subjected to the action of a saccharide-transferring enzyme to produce α-D-glycosyl kasugamycin, and then subjected to the action of a glucoamylase to produce and accumulate α-D-glucosyl kasugamycin wherein kasugamycin links to an equimolar glucose residue. Furthermore, β-amylase (EC 3.2.1.2) may be used together with glucoamylase.

The reaction mixture obtainable in this way usually contains intact kasugamycin, glucose, maltooligosaccharides and the like besides α-D-glycosyl kasugamycin. The mixture may be prepared into final products without purification.

Usually, the reaction mixture is filtered and concentrated into a syrupy product, which is then dried and pulverized into a powdery product of α-D-glycosyl kasugamycin.

Furthermore, in the case of preparing a purified α-D-glycosyl kasugamycin, for example, α-D-glycosyl kasugamycin is separated from the contaminants including glucose and oligosaccharides by utilizing the difference in adsorbability to a strongly-acidic cation exchange resin (H-form). As such a strongly-acidic cation exchange resin (H-form), for instance, a styrene-divinylbenzene copolymer resin (H-form) wherein sulfonic acid groups are linked can be used. Examples of commercially available products are "Dowex 50W-X2", "Dowex 50W-X4" and "Dowex 50W-X8" (trade names, made by Dow Chemical Co., USA), "Amberlite IR-116", "Amberlite IR-118" and "Amberlite IR-124" (trade names, made by Rohm & Hass Company, Philadelphia, USA) and "Diaion SK1B", "Diaion SK102" and "Diaion SK104" (trade names, made by Mitsubishi Kasei Corporation, Tokyo, Japan). When the reaction mixture containing α-D-glycosyl kasugamycin is applied to a column of a strongly-acidic cation exchange resin (H-form), the α-D-glycosyl kasugamycin and a relatively-small amount of the unchanged kasugamycin are adsorbed on the resin, while a large amount of water-soluble saccharides such as glucose and maltooligosaccharides pass through the column without being adsorbed.

If necessary, after completion of the saccharide-transfer reaction but before treatment with a strongly-acidic cation exchange resin, the reaction mixture may be subjected to one or more treatments for purification, for example, a treatment wherein the reaction mixture is heated and thereafter insolubilized substances are removed by filtration.

The above-mentioned column of a strongly-acidic cation exchange resin on which a large amount of α-D-glycosyl kasugamycin and a relatively-small amount of the unchanged kasugamycin have been specifically adsorbed is washed with an aqueous acidic solution such as a diluted acid and subsequently washed with an aqueous alkaline solution such as an aqueous solution of sodium hydroxide or ammonia solution. Thus, the α-D-glycosyl kasugamycin and intact kasugamycin can be eluted.

In addition the resultant eluate is concentrated to an adequate level to obtain a syrupy product mainly composed of α-D-glycosyl kasugamycin. Subsequent drying and pulverization of the product yield a powdery product mainly composed of α-D-glycosyl kasugamycin.

Also a highly purified α-D-glycosyl kasugamycin can be obtained by allowing glucoamylase together with a saccharide-tranferring enzyme to act on a solution containing kasugamycin and an amylaceous substance to form and accumulate α-D-glycosyl kasugamycin containing equimolar or more glucose residues and then applying the resultant mixture to a strongly-acidic cation exchange resin (H-form) to effect a purification.

If necessary, the reaction mixture can be treated by methods other than the above-mentioned treatment using a strongly-acidic cation exchange resin (H-form), for example, separations utilizing the difference of solubility, molecular weight fractionation, membrane separation, column chromatography, and high-performance liquid chromatography (HPLC). A more highly purified α-D-glycosyl kasugamycin can be prepared by treating the reaction mixture by a combination of one or more these methods the treatment using a strongly-acidic cation exchange resin. If necessary, the purity of α-D-glycosyl kasugamycin can be further improved by crystallizing α-D-glycosyl kasugamycin from its supersaturated solution and separating the resultant crystals.

The α-D-glycosyl kasugamycin thus obtained is readily hydrolyzable by α-glucosidase into D-glucose and kasugamycin. The released kasugamycin exhibits the same physiological activities as those of intact kasugamycin.

The α-D-glycosyl kasugamycin is used as an antibacterial agent in agriculture and gardening to prevent the growth of pathogenic microorganisms on the leaves or in the farming place of the vegetables and fruits such as melon, tomato, carrot and cabbage, including microorganisms of *Piricularia oryzae* or *Pseudomonas glumae*, the pathogenic microorganisms against rice plants. As an antibacterial agent applicable for fishery and farming, usually, α-D-glycosyl kasugamycin can be incorporated into in feeds and pet foods for domestic animal and pet fish for preventing the growth of pathogenic microorganisms.

The shape or form of the antibacterial agent can be freely chosen to meet its final use; for example, liquid preparations such as nebula, and solid preparations such as powder and granules. In such preparations one or more ingredients, for example, biologically-active substance, antibiotic, adjuvant (excipient, binder and releasing agent), bulking agent, stabilizer, coloring agent and flavoring agent, may be included in combination.

Usually the doses may be similar to the conventional one of intact kasugamycin. The dose is adequately changed depending upon the kasugamycin content, administration route and frequency of administration, usually, in the range of not more than 1,000 ppm as α-D-glycosyl kasugamycin, desirably, in the range from about 5 to about 800 ppm, and in the case of using in farm and garden or seed-bed, suitably in the range from about 0.1 to about 20.0 g per 1 $m^2$.

α-D-Glycosyl kasugamycin is incorporated in products by conventional method, for example, mixing, kneading, dissolving, soaking, penetrating, spreading, spraying and injecting, before completion of their processing.

The present invention is more specifically described and explained by means of the following Examples in which all parts are by weight unless otherwise noted. It is to be understood that the present invention is not limited to the Examples, and various changes and modifications may be made in the invention without departing from the spirit and scope thereof.

TEST EXAMPLE 1

[Production of α-D-glucosyl kasugamycin]

To a mixture of 5 g of kasugamycin (made by Sigma Chemical Company, USA), 50 g of dextrin ("PINE-DEX #1", trade name, made by Matsutani Chemical Industry Co., Ltd., Japan), 60 mg of calcium chloride and 7,000 units/g dextrin of cyclomaltodextrin glucanotransferase derived from *Bacillus stearothermophilus* (commercially available from Hayashibara Biochemical Labs., Inc., Okayama, Japan) was added 0.1M acetate buffer (pH 5.5) to adjust the volume to 100 ml. The mixture was allowed to react at 50° C. for 48 hours. Thin-layer chromatographic analysis of the reaction mixture revealed that most of the kasugamycin used was converted into α-D-glycosyl kasugamycin wherein kasugamycin was linked with equimolar or more glucose residues. To the reaction mixture was added 800 units/g solid of glucoamylase derived from *Rhizopus niveus* (commercially available from Seikagaku-Kogyo Co., Ltd., Tokyo, Japan). The mixture was allowed to react at 37° C. for 6 hours. Thin-layer chromatographic analysis of the reaction mixture revealed that it contained D-glucose, α-D-glucosyl kasugamycin and kasugamycin.

The vessel containing the reaction mixture was heated in boiling water for 10 minutes to inactivate the remaining enzyme. Thereto was added the same amount of methanol. The solution was filtered, and then the filtrate was concentrated under reduced pressure and applied to a column of a strongly-acidic cation exchange resin, "Dowex-X8 (H-form)" (commercially available from Dow Chemical Co., USA). The column was washed with 0.01N hydrochloric acid and then water to remove the impurities such as glucose. Then, α-D-glucosyl kasugamycin and intact kasugamycin were eluted with a 1% aqueous ammonia from the column. The eluate was neutralized with hydrochloric acid, concentrated in vacuo and lyophilized to obtain an pulverized α-D-glucosyl kasugamycin. The pulverized product was dissolved in water. The solution was subjected to gel-chromatography using a column packed with "Sephadex G-10" (trade name, made by Pharmacia LKB Biotechnology, Sweden) having a diameter of 5.6 cm and a length of 62 cm. Fractions being rich in α-D-glucosyl kasugamycin were collected, and then concentrated in vacuo and lyophilized to obtain a highly purified α-D-glucosyl kasugamycin powder.

The physicochemical analysis of the powder revealed that it was α-D-glucosyl kasugamycin which has been unknown up to now.

The physicochemical properties of the thus obtained α-D-glucosyl kasugamycin are shown and explained below.

(1) Thin-layer chromatographic analysis

Table 1 illustrates the results of thin-layer chromatographic analysis of α-D-glucosyl kasugamycin and kasugamycin as a comparison.

TABLE 1

| Solvent System | A | B | C |
|---|---|---|---|
| Substance | | | |
| Kasugamycin | 0.21 | 0.62 | 0.04 |
| α-D-glucosyl kasugamycin | 0.18 | 0.51 | 0.02 |

Note: Each value means Rf value.
Solvent system;
A [n-Butanol:Acetic acid:Water = 2:1:1 (by volume)]
B [Chloroform:Methanol:Ammonia (28%) = 1:3:2 (by volume)]
C [Acetonitrile:Water = 1:1 (by volume)]

(2) Infrared absorption spectrum

The KBr tablet method was used. The results was illustrated in FIG. 1.

The infrared absorption spectrum of the α-D-glucosyl kasugamycin and that of kasugamycin as a comparison were respectively designated by a solid line and a dotted line.

(3) Solubility in solvents

The α-D-glucosyl kasugamycin was readily soluble in water, acetic acid, 0.1N sodium hydroxide or 0.1N hydrochloric acid; substantially insoluble in methanol or ethanol; and insoluble in chloroform or ethyl acetate. At room temperature, the solubility of the α-D-glucosyl kasugamycin in water was not less than fivefold of that of kasugamycin.

(4) Appearance

The α-D-glucosyl kasugamycin was an odorless whitish powder. An aqueous solution of the α-D-glucosyl kasugamycin was neutral or acidic.

(5) Stability

The α-D-glucosyl kasugamycin in an aqueous solution was excellently stable at a pH in the range from 3.0 to 7.0.

(6) Color reaction

The α-D-glucosyl kasugamycin exhibited green coloration in the anthrone-sulfuric acid reaction. The result of Fehling's solution reductive reaction was negative.

(7) Structure (a) Hydrolysis

The α-D-glucosyl kasugamycin was readily hydrolyed by α-glucosidase derived from pig liver, seeds of rice plant or microorganisms of the genus Mucor to form 1 mole of D-glucose per 1 mole of kasugamycin.

(b) NMR spectrum

Figure 2A:
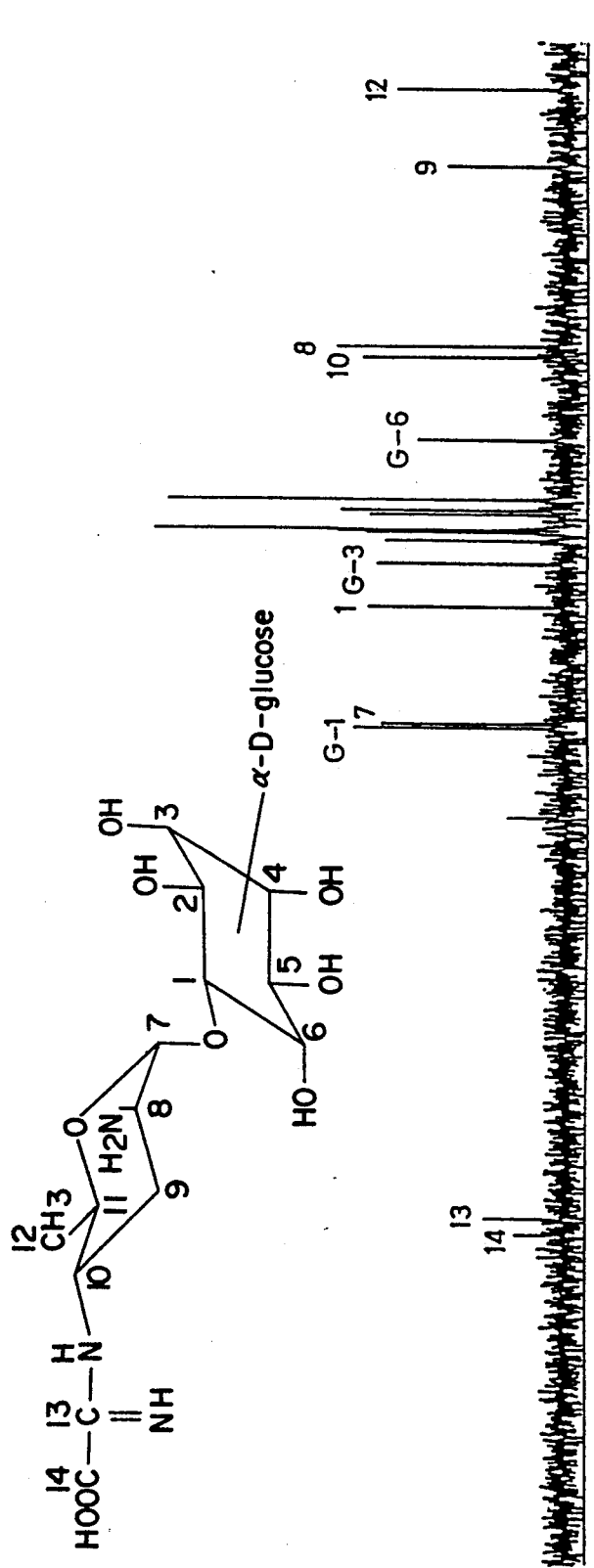
FIG. 2(A) shows a $^{13}$C-NMR spectrum of the α-D-glucosyl kasugamycin.
Figure 2B:
FIG. 2(B) shows a $^{13}$C-NMR spectrum of kasugamycin.

The NMR spectra of the α-D-glucosyl kasugamycin and kasugamycin were determined by use of an NMR spectrometer, "VXR-500" (commercially available from Varian Co., USA). The solvent was $D_2O$. The results are shown in FIG. 2. The $^{13}C$-NMR spectrum of the α-D-glucosyl kasugamycin was illustrated in (A) and that of kasugamycin as a comparison was illustrated in (B). In FIG. 2., G-1 exhibits the carbon at 1-position of α-D-glucose, G-3 exhibits the carbon at 3-position of α-D-glucose, and G-6 exhibits the carbon at 6-position of α-D-glucose.

As shown in FIG. 2, a remarkable chemical shift was found in the inositol residue of kasugamycin. Therefore it was confirmed that the transferred glucose was linked with a hydroxyl group of the inositol residue of kasugamycin via an ether bond.

The above physicochemical properties confirm that the α-D-glucosyl kasugamycin of the present invention is a novel substance having the chemical structure shown by the following formula (II):

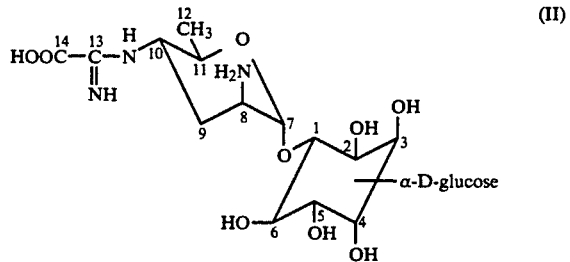

Further, these results show that the α-D-glycosyl kasugamycin of the present invention, which was obtained by allowing cyclomaltodextrin glucanotransferase to act on a solution containing kasugamycin and an amylaceous substance, and wherein equimolar or more glucose residues was linked with kasugamycin, has the chemical structure shown by the formula (III):

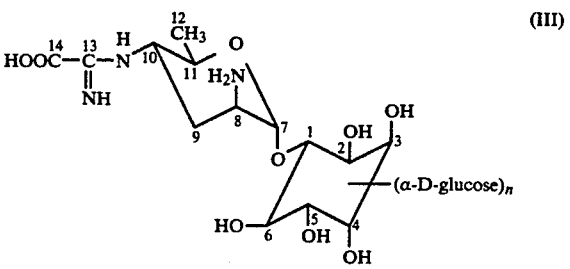

wherein n is an integer not less than 1 and D-glucoses are joined by a α1, 4 glucosidic linkage. In the case that n is 1, the formula shows α-D-glucosyl kasugamycin. In the case that n is 2, the formula shows α-maltosyl kasugamycin. In the case that n is 3, the formula shows α-maltotriosyl kasugamycin. And in the case that n is 4, the formula shows α-maltotetraosyl kasugamycin.

TEST EXAMPLE 2

[Acute toxicity]

The α-D-glucosyl kasugamycin was peritoneally administered to 7 week-old dd mice for acute toxicity test. There are not observed any deaths in any group wherein the highest does was 3,000 mg per kg body weight. From the result, it was demonstrated that the toxicity of this substance was extremely low.

TEST EXAMPLE 3

[pH Stability test of α-D-glucosyl kasugamycin]

Fifty μl of 2.56 w/v % aqueous solution of α-D-glucosyl kasugamycin (purity: about 80%), which was prepared according to the method described in Example 3 was mixed with 450 μl of a buffer adjusted to pH 2.0, 4.0, 6.0, 8.0 or 10.0. The mixture was kept at 120° C. for 1 hour in a well-closed container. As the buffer was used 1M HCl- Sodium acetate buffer (pH 2.0 or pH 4.0), 1M acetic acid buffer (pH 6.0), 1M Tris-HCl buffer (pH 8.0) or 1M NH₄OH- NH₄Cl buffer (pH 10.0).

Each of thus obtained mixtures was cooled with a running water. Then, the mixture was diluted 5 times with 0.5M Na₃PO₄-H₃PO₄ (pH 6.0). Successively, the diluted mixture subjected to HPLC under the following conditions.

As a comparison was used a sample obtained by diluting 5 times a mixture of 50 μl of 2.56 w/v % aqueous solution of α-D-glucosyl kasugamycin and 450 μl of deionized water with 0.5M Na₃PO₄-H₃PO₄ (pH 6.0).

Residue was calculated on the basis of a ratio of the peak area of α-D-glucosyl kasugamycin in each treated mixture to that in the sample as a comparison.

Also, 1.0 w/v % aquous solution of kasugamycin purchased from Hokko Kagaku Kogyo Kabushiki Kaisha was treated in the same manner as described in the case of α-D-glucosyl kasugamycin. Residue in each pH condition was calculated. The results are shown in Table 2.

Conditions for HPLC

Column: ODS-M (commercially avairable from Shimazu Techno Research Co., Ltd.)
Eluate: Acetonitrile/Water* = 8/92 (v/v)   *0.2M CH$_3$(CH$_2$)$_5$SO$_3$Na (pH was not adjusted) 0.005M Na$_3$PO$_4$-H$_3$PO$_4$ (pH 6.0)
Detection: 214 nm
Flow rate: 0.3 ml/min
Temperature: 25° C.
Sample: 20 μl

TABLE 2

| | Residue (%) | ($\bar{X}$, n = 5) |
|---|---|---|
| pH | Kasugamycin | α-D-Glucosyl kasugamycin |
| 2.0 | 76.0 | 76.2 |
| 4.0 | 72.1 | 75.2 |
| 6.0 | 26.8 | 26.9 |
| 8.0 | 9.5 | 17.6 |
| 10.0 | trace | trace |

As is clear from the results in Table 2, in case that α-D-glucosyl kasugamycin being examples of α-D-glycosyl kasugamycin and kasugamycin were treated under severe conditions of the treatment at 120° C. for 1 hour, under an alkaline condition (pH 8.0) α-D-glucosyl kasugamycin was approximately 1.85 (17.6/9.5=1.85) times stabler than kasugamycin, although they showed similar stability under a pH range from 2.0 to 6.0.

The fact that a considerable amount of the α-D-glucosyl kasugamycin remained after the treatment under very severe conditions, i.e. the treatment at 120° C., for 1 hour, at pH 8.0, reveals that the α-D-glucosyl kasugamycin has more excellent stability in comparison with kasugamycin in a conventional step of a process for preparation of agricultural chemicals containing α-D-glucosyl kasugamycin or α-D-glycosyl kasugamycin as an active ingredient, under a condition for perservation thereof, and under a condition for use thereof.

Furthermore, even in case that salts and α-D-glucosyl kasugamycin coexist in final products (in some cases, a pH locally varies), α-D-glucosyl kasugamycin is maintained stably, as well as in case of treatment with acid or with alkali in the above-mentioned step. Therefore, after spraying plants on field with the agricultural chemicals, α-D-glucosyl kasugamycin is extremely stable and fully exhibits physiological activities inherent to kasugamycin.

Therefore, it can be understood that the α-D-glycosyl kasugamycin has more excellent industrial usefulness in comparison with kasugamycin.

The following examples will illustrate the preparations and uses of the α-D-glycosyl kasugamycin of the present invention.

EXAMPLE 1

[α-D-glycosyl kasugamycin]

One part of kasugamycin (made by Sigma Chemical Co., Saint Louis, Mo., USA) and 8 parts of dextrin (DE 8) were dissolved in 40 parts of water by heating. Thereto was added 20 units/g dextrin of cyclomaltodextrin. glucanotransferase derived from *Bacillus stearothermophilus* (made by Hayashibara Biochemical Labs., Inc., Okayama, Japan). Then while keeping the solution at pH 6.0 at 65° C., the solution was allowed to react for 48 hours. Thin-layer chromatographic analysis of the reaction mixture revealed that most of the kasugamycin used was converted into α-D-glycosyl kasugamycins, wherein kasugamycin was linked with equimolar or more glucose residues, such as α-D-glucosyl kasugamycin, α-maltosyl kasugamycin, α-maltotriosyl kasugamycin and α-maltotetraosyl kasugamycin.

The reaction mixture was heated to inactivate the remaining enzyme and filtered. The filtrate was concentrated to obtain a syrupy product in a yield of about 95% (on a dry solid basis (hereinafter referred to as "d.s.b.")) based on the weight of the starting material. The syrupy product contained about 20 w/w % (d.s.b.) of α-D-glycosyl kasugamycins, and a relatively small amount of kasugamycin and a relatively large amount of dextrin.

This product can be favorably used as a high-safe antibacterial agent in agriculture, gardening, domestic animal feeding and pet fishing.

EXAMPLE 2

[α-D-glycosyl kasugamycin]

(1) Preparation of α-glucosidase

*Mucor javanicus* IFO 4570 (the Institution for Fermentation, OSAKA (IFO)) 17-35, Jusohonmachi 2- chomo, Yodogawa-Ku, Osaka, 532, Japan was inoculated and cultivated at 30° C. for 44 hours under aeration-agitation conditions in 500 parts of a liquid culture medium which contained, together with water, 4.0 w/v % of maltose, 0.1 w/v % of potassium phosphate monobasic, 0.05 w/v % of ammonium nitrate, 0.05 w/v % of potassium chloride, 0.2 w/v % of polypeptone and 1 w/v % of calcium carbonate all of which had been sterilized by heating and under sterile conditions added to the medium immediately before the inoculation.

After completion of the cultivation, the mycelia was collected from the culture. Thereto was added 500 parts of 4M solution of urea in 0.5M acetate buffer (pH 5.3) per 48 parts of the wet mycelia. Thus obtained mixture was allowed to stand at 30° C. for 40 hours and thereafter centrifuged. The supernatant was dialyzed against flowing water overnight. After addition of ammonium sulfate to give 0.9 saturation, it was allowed to stand at 4° C. overnight. The resultant sediment was collected, suspended in 50 parts of 0.01M acetate buffer (pH 5.3) and centrifuged. The supernatant was used as an α-glucosidase specimen.

(2) Preparation of α-D-glycosyl kasugamycin

Four parts of kasugamycin (made by Sigma Chemical Co., Saint Louis, Mo., USA) and 20 parts of dextrin (DE 30) were dissolved in 30 parts of water by heating. Thereto was added 10 parts of the α-glucosidase specimen obtained in the above (1). The solution was allowed to react with stirring at 55° C. while being kept at pH 6.5 for 40 hours.

Thin-layer chromatographic analysis of the reaction mixture revealed that most of the kasugamycin used was converted into α-D-glycosyl kasugamycins such as α-D-glucosyl kasugamycin, α-D-maltosyl kasugamycin and α-D-maltotriosyl kasugamycin. The reaction mixture was heated to inactivate the remaining enzyme and filtered. The filtrate was applied to a column of a strongly-acidic cation exchange resin (H-form), "Diaion SK-1B" (trade name, made by Mitsubishi Chemical Industries Ltd., Tokyo, Japan) at a flow rate of SV (Space Velocity) 2. As a result, a large amount of α-D-glycosyl kasugamycins and a relatively-small amount of kasugamycin were specifically adsorbed on the cation exchange resin, while glucose and oligosaccharide passed through the column without being adsorbed. Thereafter, the column was washed with an acidic water. Then α-D-glycosyl kasugamycins and the remaining kasugamycin were eluted from the column with an aqueous ammonia. The resultant eluate was concentrated under reduced pressure and subsequently dried and pulverized to obtain a powdery product composed of α-D-glycosyl kasugamycins together with kasugamycin in a yield of about 90% based on the weight of the starting kasugamycin (d.s.b.).

This product can be favorably used as a highly-safe antibacterial agent in agriculture, gardening, domestic animal feeding and pet fishing.

EXAMPLE 3

[α-D-glucosyl kasugamycin]

One part of kasugamycin (made by Sigma Chemical CO., Saint Louis, Mo., USA) and 10 parts of dextrin (DE 12) were dissolved in 15 parts of water by heating. Thereto was added with 20 units/g dextrin of cyclomaltodextrin glucanotransferase (made by Hayashibara Biochemical Labs., Inc., Okayama, Japan). Thereafter the solution was allowed to react for 48 hours under stirring condition while being kept at pH 6.0 at 70° C. Thin-layer chromatographic analysis of the reaction mixture revealed that most of the kasugamycin used was converted into α-D-glycosyl kasugamycins wherein kasugamycin is linked with equimolar or more glucose residues. In the similar manner as described in Example 1, the reaction mixture was heated to inactivate the remaining enzyme and adjusted pH 5.0 and after addition of 100 parts of glucoamylase (made by Seikagaku-Kogyo Co., Ltd., Japan) per g of d.s.b., the resultant was allowed to react at 50° C. for 5 hours.

The reaction mixture was heated to inactivate the remaining enzyme and filtered. The filtrate was applied to a column of a strongly-acidic cation exchange resin (H-form), "Amberlite IR-116" (trade name, made by Rohm & Hass Company, Philadelphia, USA) at a flow rate of SV 1.5. As a result, the resin adsorbed α-D-glucosyl kasugamycin and remaining kasugamycin both present in the reaction mixture, while glucose passed through the column without being adsorbed. The column was washed with an acidic water. Then α-D-glucosyl kasugamycin and intact kasugamycin were eluted from the column with an aqueous ammonium. The resultant eluate was concentrated under reduced pressure and subsequently dried and pulverized to obtain a powdery product composed of α-D-glucosyl kasugamycin together with kasugamycin in a yield of about 80% (d.s.b.) based on the weight of the starting kasugamycin.

This product is favorably used as a high-safe antibacterial agent in agriculture, gardening, domestic animal feeding and pet fishing.

EXAMPLE 4

[Water-dispersible powder]

Ten parts of the syrupy product containing α-D-glycosyl kasugamycin prepared in Example 1, 2 parts of white carbon, 3 parts of sodium dodecylbenzene sulfonate, 2 parts of sodium lignin sulfonate and 90 parts of clay were mixed. The mixture was pulverized to give a water-dispersible powdery product containing α-D-glycosyl kasugamycin.

This product is used as a dispersion which is prepared by dispersing one part of the product in about 500 to about 1000 parts of water. When the dispersion is used by spraying in the range from 100 to 150 liters per are of rice planting farm, fungal diseases of rice can be prevented.

EXAMPLE 5

[Dusting powder]

There were mixed uniformly 0.3 part of the powdery product containing α-D-glycosyl kasugamycin powder prepared in Example 2, 90 parts of talc and 5 parts of white carbon. The mixture was pulverized to give a dusting product.

When the product intact is used by dusting in the range from about 2 to about 4 kg per are of rice planting farm, fungal diseases of rice can be prevented.

EXAMPLE 6

[Granules]

Two parts of the powdery product containing α-D-glycosyl kasugamycin prepared in Example 3, 3 parts of sodium lignin sulfonate, 2 parts of sodium lauryl sulfate and 90 parts of clay were mixed and kneaded. The mixture was granulated. The resultant was dried and screened to give a granular product.

When the product intact is used in the range from about 2 to about 4 kg per are of rice planting farm, fungal diseases of rice can be prevented.

In addition to the ingredients used in the Examples, other ingredients can be used in the Examples as set forth in the specification to obtain substantially the same results.

What we claim is:

1. An α-D-glycosyl kasugamycin having the formula (III) which is hydrolyzed by α-glucosidase (EC 3.2.1.20) into one or more moles of D-glucose per 1 mole of kasugamycin:

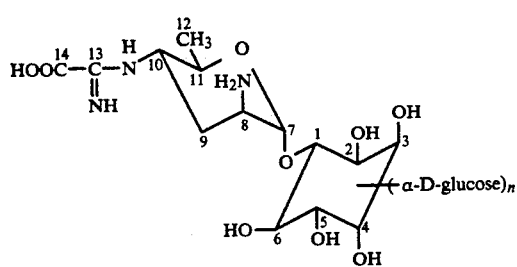

wherein n is an integer of not less than 1.

2. The α-D-glycosyl kasugamycin of claim 1, which is a α-D-glucosyl kasugamycin having the formula (II):

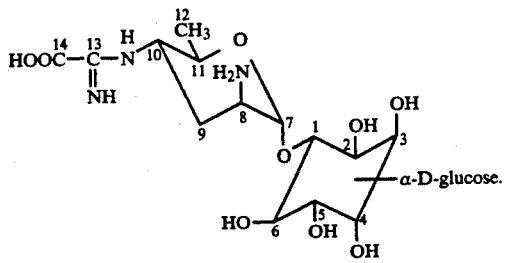

3. An α-D-glycosyl kasugamycin according to claim 1 made by the process comprising the steps of:
    (1) dissolving 1 to 4 parts of kasugamycin and 8 to 20 parts of dextrin in 15 to 40 parts of water;
    (2) adding an enzyme to said solution, wherein said enzyme is a saccharide transferring enzyme;
    (3) reacting said solution of kasugamycin and dextrin for a period of about 5 to 80 hours, at a temperature of about 10° to 90° C., and a pH of about 3.0 to 7.0;
    (4) inactivating said enzyme by heating; and
    (5) filtering said reaction mixture through a column of a strong acidic cation exhange resin to obtain α-D-glucosyl kasugamycin.

4. An α-D-glycosyl kasugamycin according to claim 2 made by the process comprising the steps of:
    (1) dissolving 1 to 4 parts of kasugamycin and 8 to 20 parts of dextrin in 15 to 40 parts of water;
    (2) adding an enzyme to said solution, wherein said enzyme is a saccharide transferring enzyme;
    (3) reacting said solution of kasugamycin and dextrin for a period of about 5 to 80 hours, at a temperature of about 10° to 90° C., and a pH of about 3.0 to 7.0;
    (4) inactivating said enzyme by heating; and
    (5) filtering said reaction mixture through a column of a strong acidic cation exhange resin to obtain α-D-glucosyl kasugamycin.

* * * * *